(12) United States Patent
Narciso et al.

(10) Patent No.: US 8,424,243 B1
(45) Date of Patent: Apr. 23, 2013

(54) USE OF COATED PROTECTIVE AGENT TO PROTECT HORTICULTURAL CROPS FROM DISEASE

(75) Inventors: Jan Narciso, Winter Haven, FL (US); Robert Fassel, Nachos, WA (US); Lawrence E. Schrader, Wenatchee, WA (US)

(73) Assignees: The United States of America as Represented by Secretary of Agriculture, Washington, DC (US); Pace International LLC, Seattle, WA (US); Washington State University Research Foundation, Pullman, WA (US)

( * ) Notice: Subject to any disclaimer, the term of this patent is extended or adjusted under 35 U.S.C. 154(b) by 77 days.

(21) Appl. No.: 12/862,398

(22) Filed: Aug. 24, 2010

Related U.S. Application Data

(63) Continuation-in-part of application No. 11/737,405, filed on Apr. 19, 2007, which is a continuation of application No. 10/703,105, filed on Nov. 6, 2003, now Pat. No. 7,222,455, which is a continuation-in-part of application No. 09/830,529, filed as application No. PCT/US99/25350 on Oct. 26, 1999, now Pat. No. 6,857,224.

(60) Provisional application No. 60/106,059, filed on Oct. 27, 1998.

(51) Int. Cl.
*A01G 13/00* (2006.01)
*A01N 1/00* (2006.01)

(52) U.S. Cl.
USPC .................. 47/58.1 FV; 47/24.1; 47/2

(58) Field of Classification Search ............ 47/58.1 FV, 47/58.1 R, 23.1, 23.2, 24.1, 2
See application file for complete search history.

(56) References Cited

U.S. PATENT DOCUMENTS

| | | | | |
|---|---|---|---|---|
| 3,997,674 A | * | 12/1976 | Ukai et al. | 426/90 |
| 4,771,571 A | * | 9/1988 | Obrero et al. | 47/58.1 R |
| 4,857,344 A | * | 8/1989 | Obrero et al. | 426/308 |
| 5,052,618 A | * | 10/1991 | Carlon et al. | 239/77 |
| 5,369,099 A | * | 11/1994 | Iverson et al. | 514/108 |
| 6,092,329 A | * | 7/2000 | Hoshino | 47/24.1 |
| 6,857,224 B1 | * | 2/2005 | Kammereck et al. | 47/58.1 FV |
| 7,222,455 B2 | * | 5/2007 | Schrader | 47/58.1 FV |
| 7,267,743 B2 | * | 9/2007 | Borsinger et al. | 162/5 |

FOREIGN PATENT DOCUMENTS

| | | | |
|---|---|---|---|
| ES | 2072822 A1 * | 7/1995 | |
| FR | 2883003 A1 * | 9/2006 | |
| JP | 51048456 A * | 4/1976 | |

* cited by examiner

*Primary Examiner* — Kristen C Hayes
(74) *Attorney, Agent, or Firm* — Merchant & Gould, P.C.

(57) ABSTRACT

Disease, sunburn and insect damage to fruit and vegetable crops is significantly reduced by treatment of both fruit and foliage with a preventative amount of a protective agent (such as copper sulfate or hydroxide) and an optional amount of thixotropic smectic clay material, chemically altered to render its surface lipophilic, which are combined with a wax emulsion comprising a matrix of complex hydrocarbons, an emulsifying agent and water. In the practice of this disclosure the disease, sunburn, and insect protective composition is further diluted in an aqueous solution that is sprayable by commercial applicators.

12 Claims, No Drawings

USE OF COATED PROTECTIVE AGENT TO PROTECT HORTICULTURAL CROPS FROM DISEASE

CROSS-REFERENCE TO RELATED APPLICATION

This application is a continuation-in-part of application Ser. No. 11/737,405 filed Apr. 19, 2007, which is a continuation of U.S. application Ser. No. 10/703,105 now U.S. Pat. No. 7,222,455, filed Nov. 6, 2003, which is a continuation-in-part of U.S. application Ser. No. 09/830,529 now U.S. Pat. No. 6,857,224 filed Jul. 30, 2001 which is a National Stage Entry of PCT/US99/25350 of Oct. 26, 1999, which claims priority of the provisional application 60/106,059, filed Oct. 27, 1998.

FIELD OF THE INVENTION

The disclosure relates to protectively coated fruits and vegetables, and methods for the treatment of plants that reduces the incidence and extent of disease.

BACKGROUND

Crops, including orchard/grove-grown fruit, are typically exposed to numerous perils while being grown which result in reduction of crop quality and unsalable commodities. Such perils include exposure to adverse weather, predators, pathogens, and the like. Various chemical formulations (e.g. sprays, dusts) have been developed to reduce the negative effects of many of these threats and these formulations can function as mechanical and/or chemical barriers. However, each of these formulations is rather limited to helping a relatively narrow subset of the negative effects of these perils; and each of the formulations is often relatively expensive or introduces other unintended consequences such as health hazards to humans or environmental pollution.

Sekutowski et al. (U.S. Pat. No. 5,908,708) developed a protective water resistant coating that was formulated as an aqueous dispersion of particulate matter having a hydrophobic outer surface in a low boiling point organic liquid, such as methanol. The particulate matter of the Sekutowski et al. coating can be any finely divided hydrophobic particulate solids including minerals, such as calcium carbonate, mica, talc, kaolin, bentonites, clays attapulgite, pyrophyllite, wollastonite, silica, feldspar, sand, quartz, chalk, limestone, precipitated calcium carbonate, diatomaceous earth and barytes. One agricultural use of the Sekutowski et al. aqueous dispersions is to provide tree leaves with a water resistant coating by spraying the formulation onto the surface of the leaves. The water resistant coating is thought to reduce plant disease and insect damage. However, one major problem with the Sekutowski et al. formulation is the use of large volumes of organic liquids such as alcohols, ketones and cyclic ethers that are highly flammable and pose other health risks to workers during spray application.

Applications of mechanical-protective formulations which additionally function as pesticides (chemical protectants) in plant crops would be a valuable addition to Integrated Pest Management (IPM) practices providing "soft" suppression of pests without disrupting natural control processes. Desirable formulations would be expected to be non-toxic to mammals and thus safe for applicators and farm workers. Application of the protective formulations by commonly employed horticultural spray operations invariably involves extensive treatment of foliage and fruit or vegetable. It is therefore important to develop new formulations that have protective properties against disease to fruits and vegetables as well as against damage caused by insects that inhabit and attack both foliage and fruit.

In addition to pathogen and insect damage, sunburn has been a problem for apple growers (and other commodities as well) for at least 75 years, but its incidence has increased in recent years with the widespread use of dwarfing rootstocks and high-density plantings. Many apple cultivars (e.g., 'Fuji,' 'Granny Smith,' 'Jonagold,' 'Gala,' and 'Braeburn') are susceptible to sunburn. Prominent growers have indicated that sunburn may be the most significant cullage or quality problem in the industry. Trees are smaller and fruit are more exposed to solar radiation making fruit more susceptible to sunburn.

In summary, there is a lack of adequate means to economically prevent damage to fruit and vegetable crops. Thus, there is a strong need in agricultural markets for an inexpensive and effective composition that prevents or inhibits disease, repels deleterious insects, protects from sunburn, is long lasting, and is relatively amenable to easy application by growers and commercial applicators.

SUMMARY OF THE INVENTION

This summary is provided to introduce a selection of concepts in a simplified form that are further described below in the detailed description. This summary is not intended to identify key features or essential features of the claimed subject matter, nor is it intended as an aid in determining the scope of the claimed subject matter.

A spray of a wax formulation combined with a copper formulation for the control of fungal and bacterial pathogens on fruit is disclosed. The disclosed spray can be used commercially to treat, for example, fruit (including citrus) to protect the fruit against a combination of perils such as both fungal and bacterial disease, sunburn, and insect damage.

It has now been discovered that various problems can be overcome by the present invention, such as the bacterial and fungal disease that often occurs in citrus, other fruit, and vegetable crops that receive excessive rainfall during critical growing periods when there is an abundance of young tissue available. Such problems can be significantly reduced by treating the crop with an effective amount of a plant protective coating composition of the present disclosure.

An effective amount of a plant protective agent and coating composition of the disclosure is defined as any amount of the disclosed protective composition that upon application to the surface of a fruit or vegetable results in the measurable reduction of the incidence of damage by bacterial diseases (such as citrus canker) or fungal diseases (such as melanose and blackspot) to fruit or vegetables. The plant protective agent and coating compositions of the disclosure also form a barrier that reduces insect-inflicted damage and/or sunburn to the fruit or vegetable.

In one aspect, the present disclosure provides a fruit or vegetable that is protectively coated with a plant protective composition comprising a protective agent and lipophilic thixotropic smectic clay suspended in a sticking agent (such as a wax emulsion). The protective agent can be a fungicide and/or bactericide (such as copper formulations of sulfates, hydroxides and other prophylactics). The wax emulsion preferably comprises complex hydrocarbons (also known as a matrix of hydrocarbons), at least one emulsifying agent and water. In a presently preferred embodiment of the present disclosure, both an anionic lipophilic hydrophilic emulsifier and a cation hydrophilic emulsifier are used to emulsify the matrix of hydrocarbons. Preferably, the protective agent is a mixture of about 2.37 grams/Liter (weight/volume) of copper formulation that is a mixture comprising 46% (weight/ weight) active copper hydroxide, and about 0.5 to 10% (weight/weight) of (optional) lipophilic thixotropic smectic clay dispersed in about 90 to 99.5% (weight/weight) of the wax emulsion. Preferably, the protective agent is also a mixture of about 0.05 to 1.0% (weight/volume) of copper formulation (comprising copper hydroxide or copper sulfate, for example), and about 0.5 to 10% (weight/weight) of (optional) lipophilic thixotropic smectic clay dispersed in about 90 to 99.5% (weight/weight) of the wax emulsion. For some uses of the disclosed composition it is preferable to dilute the mixed composition into an aqueous solution. Preferably, the compositions of the disclosure are diluted into an aqueous solution in a volume/volume ratio of between about 1 part plant protective composition to about 1 part aqueous solution to about 1 part plant protective composition to about 10 parts aqueous solution.

Preferred plant protective coating compositions are sprayable onto fruit trees, vegetable crops and the like by a wide variety of commercial agricultural applicators. The matrix of hydrocarbons helps to maintain the physical integrity of the clay film and copper formulations on the fruit surface making the formulation more durable and resistant to rain wash. Because the plant protective coating compositions, when applied as finely dispersed spray particles, cover both foliage and fruit, a dual beneficial effect is achieved through prevention of the incidence of disease (such as canker and melanose) and damage by insects. The physical integrity of the clay film, as well as the matrix of hydrocarbons on foliage and fruit surfaces also provide an effective protective barrier against sunburn and harmful insects that may naturally reside on both foliage and fruit.

In the practice of the disclosure, proper dilution of the disclosed composition in an aqueous solution allows effective spray application of the disease and insect protective material onto fruits or leaves prior to conditions that lead to the incidence of fruit disease or insect damage. The disclosed composition is preferably sprayed onto plants at a rate of about 100 to 500 gallons per acre. As compared to other formulations and treatments used to prevent disease in fruits, the disclosed compositions and methods of application significantly reduce the incidence of citrus diseases caused by bacteria and fungi.

Reduction of bacterial inoculums in citrus groves is possible by controlling the incidence of canker lesions on fruit. Controlling the incidence of canker lesions on fruit would open markets to markets that quarantine such fruit that have been grown in areas susceptible to canker or melanose. The ability to reduce the incidence of the canker inoculums would likely open markets due to the presence of a suitable prophylactic for canker. The formerly closed markets may be opened to a point where they could "live with" an occasional lesion in imported fruits. Presently, the majority of the fruit in many groves carry a substantial number of canker lesions and the practice of using copper with no fixative has not improved the fruit condition or slowed the progress of disease over the years. Fixatives presently used, such as oils, when mixed with copper compounds can cause damage to fruit rinds in hot weather. An alternative sticking agent is desired.

These and other features and advantages will be apparent from a reading of the following detailed description. It is to be understood that both the foregoing general description and the following detailed description are explanatory only and are not restrictive. Among other things, the various embodiments described herein may be embodied as methods, devices, or a combination thereof. The disclosure herein is, therefore, not to be taken in a limiting sense.

DETAILED DESCRIPTION

In arboreal growing areas having climates similar to the State of Florida in the United States, the citrus industry is contending with diseases such as citrus canker, melanose, and blackspot. Citrus canker is a disease caused by a bacterium that produces lesions on the fruit, often rendering them unmarketable and subjecting them to quarantine in certain national and international markets.

The bacterium (*Xanthomonas citri* subsp. *citri*, or Xcc) that causes citrus canker is spread chiefly by wind and rain, and can be only partially controlled by applying copper formulation sprays. All too often, frequent summer rains in growing areas (such as in the Southeast of the United States) wash the copper residue off the fruit and leaves of the citrus trees at times when they are most vulnerable to the disease.

Presently, the majority of the fruit in many groves in Central and South Florida carry a substantial number of canker and melanose lesions. The practice of using copper with no fixative has not effectively improved the fruit condition or slowed the progress of such diseases over the years. The disclosed composition of the spray contains a sticking agent such as a wax that is impervious to erosion by rain and is retained on the plant. By combining the wax and the copper in a single spray, the copper is affixed to the fruit and plant leaves by the wax, such that the bacteriostatic capability of the copper surprisingly remains despite rain or overhead irrigation.

Preliminary data of experimental tests show that an incidence of canker was significantly reduced with the application of the wax and copper pesticide (e.g., copper sulfate) when compared with the control fruit.

Melanose is a fungal disease that afflicts all parts of the tree and developing citrus fruit, typically in the earlier stages, causing extensive areas of diseased pustules where water droplets are deposited, especially on the fruit peel.

The disease is caused by the fungus *Diaporthe citri* Nitschke (anamorph *Phomopsis citri* (Sacc) Bubák nom..cons). The fungus usually grows superficially on the citrus fruit, and on twigs and leaves as well. Control of the disease is typically accomplished by pruning of dead wood from the trees, as well as by using agricultural sprays of copper formulations. The timing of the spraying is important and requires labor-intensive multiple re-sprayings because protection is needed on the wet plant tissues. The disease of melanose, a citrus disease that makes the fruit unmarketable, has also been significantly reduced by application of the disclosed wax and copper (e.g., copper sulfate) formulation in experimental tests (see Table 1 below).

Table 1 illustrates the significance of wax (type 3035) and Cu formulation spray-on canker and melanose reduction as compared with no spray (Control) and Cu alone with no wax sticking agent:

TABLE 1

| Canker | | versus | | p-value (significance) |
|---|---|---|---|---|
| | Wax + Cu | | Cu | 0.0035 |
| | Wax + Cu | | Cu | 0.001 |
| | Cu | | Control | 0.157 |
| Melanose | | | | |
| | Wax + Cu | | Cu | 0.001 |
| | Wax + Cu | | Cu | 0.001 |
| | Cu | | Cu | 0.001 |

In another embodiment, the disclosed technologies can be implemented by first spraying a copper pesticide formulation on the fruit and leaves of a plant to be protected, and then followed with an application of a wax formulation (that either contains or does not contain the disclosed smectic clays, for example). However, this method would typically require more man-hours and expend around twice the use of fuel and equipment as compared with using the disclosed spraying methods that use the disclosed wax and copper formulations. By using this method of control with a copper formulation and a wax adjuvant, it is often possible to apply fewer sprayings to obtain the same relief. Fewer sprayings are often achieved because the disclosed wax formulation prevents the sprayed copper formulation on the tree from being washed off by rain (for example), and which protects the surrounding soils from accumulating copper from repeated sprayings.

Experimental studies for one season surprisingly showed that by using the disclosed methods and compositions, diseases (such as canker) were significantly reduced when compared to trees with just a copper spray or with no protection at all (FIG. 4). The experimental studies also showed reduced occurrence of certain fungal diseases such as melanose. Fruit with melanose lesions is not normally used for fresh market sales. Thus, use of the disclosed methods and compositions present an opportunity for cost savings to growers. Also, the use of the disclosed wax used as a sticking agent (which reduces both the amount of copper applied and the number of sprayings and thus reduces cost), also reduces the potential for environmental contamination and buildup of copper in the soil. Thus, a reduction in spraying costs and an increase of saleable fruit is made possible.

As discussed above, certain of the disclosed embodiments can be used to simultaneously protect against disease and also sunburn. Two types of sunburn exist in apples. One is a lethal phenomenon that leads to a necrotic area on the fruit. Such fruit often becomes cullage. This phenomenon can occur when the sun-exposed side of apple skin reaches a temperature of 52 degrees plus-or-minus 1 degree Celsius for only 10 minutes. The second type of sunburn is a sublethal phenomenon that typically leads to a browning of the apple skin (sometimes referred to as "buckskin") These apples can be sold, but at a lower grade and price.

Solar light contains ultraviolet, visible, and infrared radiation. All fruits and vegetables which develop a yellow or red coloration as part of their growth cycle require a certain quantity of ultraviolet and visible light to achieve the desired maturation color. Infrared light predominantly leads to excessive heating and associated damage to fruit surfaces. The plant protective compositions of the present disclosure selectively filter out the infrared portion of solar light but allow other light components to pass. The clay coating of the disclosed spray is thus invisible to the unaided eye. In contrast, kaolin based formulations appear on the surface of sprayed fruits and leaves as a whitish-gray dust, which uniformly reflects all components of solar light, therefore depriving the developing fruit of the beneficial aspects of solar light, thus impairing photosynthesis which is necessary for plant health and quality fruit production.

In one aspect, the present disclosure provides a fruit or vegetable that is protectively coated with a composition comprising a protective agent (such as copper compounds or other pesticides), lipophilic thixotropic smectic clay, and a wax emulsion. The wax emulsion comprises a matrix of complex hydrocarbons, at least one emulsifier agent and water. Preferably, the wax emulsion contains two emulsifying agents: an anionic lipophilic emulsifier and an ionic hydrophilic emulsifier. Preferably, each emulsifier is present in the wax emulsion at a concentration of between about 1-15% (weight/weight).

In another aspect, the present disclosure provides a method of protecting fruit and vegetables from fungal and/or bacterial disease and sunburn, comprising treating a fruit or vegetable with a cupric formulation (such as copper sulfate), a sunburn preventative amount of a plant protective composition comprising lipophilic thixotropic smectic clay, and a wax emulsion. The wax emulsion is composed of a matrix of complex hydrocarbons, at least one emulsifier agent and water. Preferably, the composition is applied to the fruit or vegetable multiple times through the growing season.

In yet another disclosed embodiment, a method of plant protection is provided, comprising treating a plant with an insect-controlling amount of a plant protective composition comprising a protective agent (such as imidacloprid or copper sulfate), a lipophilic thixotropic smectic clay, and a wax emulsion. The wax emulsion is composed of a matrix of complex hydrocarbons, at least one emulsifier agent and water.

The compositions and methods of the disclosure significantly decrease the incidence of both types of sunburn in apples. The plant protective compositions are preferably based on a thixotropic smectic clay material that is chemically altered to render its surface lipophilic. Thixotropic clays, in their original form are typically hydrophilic. In order to increase the ability of the protective compositions of the disclosure to adhere to the lipophilic surface of fruit, the clay is rendered lipophilic, such as, for example, by transformation by a chemical reaction of the clay with quaternary ammonium compounds in which the ligands consist entirely of aliphatic long-chain hydrocarbons or of a mixture of aliphatic and aromatic hydrocarbon residues. This reaction converts the hydrophilic clay into a hydrophobic and lipophilic material that is capable of molecularly dispersing oils, waxes and other lipid-like materials including organic solvents. Suitable thixotropic clay materials for use in the practice of the disclosure include clays that have been transformed by a chemical reaction of the clay with quaternary ammonium compounds and have a clay structure that weakens when subjected to shear forces and increases in strength upon standing. Many thixotropic smectic clays suitable for use in the practice of the present disclosure are commercially available through a variety of vendors.

As used herein, the term "smectic clay" material refers to a Bentonite, platelet-type clay. When transformed to render it lipophilic, this clay may also be referred to as "organoclay".

The successful functioning of the disclosed disease and sunburn protectant requires a matrix consisting of complex hydrocarbons which renders the formulation sprayable by commercial agricultural applicators, maintains the physical integrity of the clay on fruit, and allows passage of visible solar radiation needed for fruit color formation but reflects undesired solar infrared light. The wax emulsion is formed by emulsifying natural or synthetic waxes with at least one emulsifying agent. Preferably, both an anionic lipophilic emulsifier and an ionic hydrophilic emulsifier are used to emulsify the matrix of hydrocarbons. The wax emulsion in the protective compositions of the present disclosure is intended to replace and enhance the properties of the natural wax layer which exists on the surface of all fruits and vegetables.

As used herein, the term "matrix of complex hydrocarbons" refers to a lipid based matrix that is capable of absorbing and dispersing the lipophilic organoclay. Suitable complex hydrocarbons for use in the present disclosure include, for example, natural and synthetic waxes that are suitable for human consumption, with melting temperatures that are higher than the melting temperatures of the target fruit or vegetable waxes. In a presently particularly preferred embodiment, the complex hydrocarbons of the present application is Carnauba Wax of a tropical origin. It contains a mixture of true waxes with long chain fatty acids and long chain esters. The fatty acid composition is complex but well represented by the term "Carnauba Wax" (*Corypha cerifera*). It will be apparent to those skilled in the art that other edible plant-derived waxes, such as Candelilla Wax (*Euphorbia cerifera* and *Pedilantus pavonis*), Alfa (*Stipa Tenacessima*), or mixtures thereof, can also be useful for this purpose. In addition, other natural wax mixtures well known in the art, such as montan wax, rice-bran wax, beeswax, Japan wax and mixtures thereof can also be used in the plant protective compositions of the present disclosure. It is also apparent that any edible synthetic waxes containing oxygen can also be used to practice the present disclosure. See, for example, the description of synthetic oxygen containing waxes in U.S. Pat. No. 5,049,186, incorporated herein by reference.

The wax emulsion of the present disclosure can be made by emulsifying the matrix of hydrocarbons with an amount of an emulsifying agent sufficient to emulsify the matrix of hydrocarbons. In this regard, a large number of different emulsifier agents can be used to prepare the wax emulsion used in the practice of the present disclosure. See for example the emulsifying agents described in U.S. Pat. Nos. 5,049,186 and 5,165,915, both of which are incorporated herein by reference. Preferably, both an anionic lipophilic emulsifier and an ionic hydrophilic emulsifier are mixed with the matrix of hydrocarbons in an amount sufficient to emulsify the edible waxes. Preferably, the anionic lipophilic and the ionic hydrophilic emulsifiers are each present in the wax emulsion at a concentration of between about 1-15% (weight/weight) relative to the matrix of hydrocarbons.

The anionic lipophilic surfactants employed in the practice of the disclosure have, preferably, a hydrophilic-lipophilic balance (HLB) ranging from about 10 to 40. They are principally salts of fatty acids (for example alkaline salts or organic salts such as amine salts), the said fatty acids having, for example, from 12 to 18 carbon atoms, and being able to have a double bond as in the case of oleic acid; the alkaline salts or salts of organic bases of alkyl-sulfuric and alkyl-sulfonic acids having 12 to 18 carbon atoms, of alkyl-aryl-sulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. Preferred anionic hydrophilic surfactants are the fatty acids oleic acid and stearic acid.

Presently preferred ionic hydrophilic surfactants include amine compounds such as ethanolamine, diethanolamine, triethanolamine, alkyl alcohol amines such as methyl-ethanolamine, butyl-ethanolamine, morpholene and mixtures thereof.

The presently preferred wax emulsion for use as the wax emulsion in the plant protective coating composition of the present disclosure is APL-BRITE 310 C produced by Solutec Corporation (Yakima, Wash.). Other commercially available material suitable for use in the disclosed protective coating composition are: Decco 231 produced by Elf-Atochem North America (Philadelphia, Pa.); Johnson's H.S and Johnson 31 produced by S.C. Johnson Wax (Racine, Wis.); and Shield Brite AP50C and Carnauba Gold produced by Pace International LLC (Seattle, Wash.).

A presently preferred material which meets the requirements specified for a chemically altered thixotropic smectic clay is Tixogel® that can be commercially obtained from Sud-Chemie Rheologicals, a division of United Catalysts Inc. of Louisville, Ky. Tixogel® is presently employed as an additive to a wide range of products including cosmetics, but not to our knowledge for any treatments of fruits or vegetables and not in combination with a matrix of complex hydrocarbons. A person with skill in the art will appreciate that many other organoclay materials having the required clay properties exist. Representative examples of useful clay materials include: numerous Tixogel and Optigel products, also produced by Sud-Chemie Rheologicals; the Bentone line of organoclays, obtainable from Rheox, Inc. (Highstown, N.J.); organoclays produced by Southern Clay Products (Gonzales, Tex.) and, the Vistrol and Organotrol lines of organoclays, sold by CIMBAR Performance Minerals (Cartersville, Ga.). The distinguishing property of the thixotropic organoclays used in the present disclosure is that they must be lipophilic.

For proper formulation of the disclosed compositions it is essential to effect an activation of the organoclay (Tixogel® MP 100) with the wax emulsion (APL-BRITE 310 C) prior to dilution with water. A mixture of about 0.5 to 7% (weight/weight) Tixogel® MP 100 in APL-BRITE 310 C can be made at room temperature by mechanical stirring, but above about 7% (weight/weight) the mixture will quickly turn into a solid gel. Preferably, the plant protective composition is a mixture of about 5% (weight/weight) of Tixogel® MP 100 in about 95% (weight/weight) APL-BRITE 310 C. The resulting protective coating material contains thixotropic clay suspended in a sprayable wax emulsion. The ratio of thixotropic smectic clay to wax emulsion may change if products other than Tixogel® MP 100 or APL-BRITE 310C are employed as the organoclay and wax emulsion, respectively.

More generally, the plant protective composition of the present disclosure is a mixture of about 0.5 to 10% (weight/weight) lipophilic thixotropic smectic clay dispersed in about 90 to 99.5% (weight/weight) of the wax emulsion. Preferably, the plant protective composition is a mixture of about 3% to 7% (weight/weight) lipophilic thixotropic smectic clay dispersed in about 97 to 93% (weight/weight) of the wax emulsion. Most preferably, plant protective composition is a mixture of about 5% (weight/weight) lipophilic thixotropic smectic clay dispersed in about 95% (weight/weight) of the wax emulsion.

The wax emulsion comprises about 5% to 10% (weight/weight) natural wax or edible synthetic oxygen containing wax, about 2% to 30% (weight/weight) emulsifying agent and about 60 to 93% (weight/weight) water. Preferably, the emulsifying agent comprises about 1 to 15% (weight/weight) anionic lipophilic emulsifier, such oleic acid, and about 1 to 15% (weight/weight) ionic hydrophilic emulsifier, such as morpholene. When the anionic lipophilic emulsifier is oleic acid and the ionic hydrophilic emulsifier is morpholene, it is most preferable that morpholene be used at a molar ratio, relative to oleic acid, that is larger than about 1.0. Most preferably, the wax emulsion comprises about 5 to 10% (weight/weight) natural wax selected from the group consisting of Carnauba wax, Candelilla wax, Alfa wax, montan wax, rice-bran wax, beeswax, Japan wax and mixtures thereof, about 2 to 7% (weight/weight) oleic acid, about 2 to 7% (weight/weight) morpholene and about 76 to 91% (weight/weight) water.

The plant protective coating composition can be applied directly onto plants or it may be diluted in an aqueous solution in any ratio which accommodates the desired field spray technique. Suitable ratios for use of the present disclosure include, for example, dilution of the protective coating mixture into an aqueous solution in a volume/volume ratio of from about 1 part protective coating mixture to about 1 part aqueous solution to about 1 part protective coating mixture to 10 parts aqueous solution. In most applications for apple and pear fruit, the rate of spray volume ranges from 100 to 400 gal/acre. The number of spray applications per growing season is also variable but ranges from one application up to ten applications depending upon weather conditions. A person skilled in the art will appreciate that the above mentioned rates would be expected to change to a minimal degree if the disclosed composition were applied to other fruits and vegetables, except that there would be a greater variation in final mixture/water ratios due to the specific requirements of agricultural crops involved, i.e. row crops, perennial trees, etc.

EXAMPLE 1

The beneficial effects of a representative protective composition of the disclosure in decreasing both types of sunburn in field trials on 'Jonagold' apples are shown in Table 2. The composition was 5% w/w of Tixogel® MP100 in APL-BRITE 310 C (hereafter PFT-X). PFT-X was applied at full strength onto apple fruits. A single application of the protectant was made to 'Jonagold' apples at Wenatchee, Wash. in mid-July. At the time of application no sunburn was observed on developing fruit. There was only one severe heat spell of sufficient intensity to cause the majority of sunburn during the season. It occurred during the first week of August. On August 19, apples treated with PFT-X surprisingly had significantly less ($P<0.05$) sunburn necrosis and sunburn browning than did untreated control fruits. On September 10, sunburn necrosis was surprisingly significantly lower in treated apples. The incidence of the necrosis type of sunburn was surprisingly decreased by 66% on fruits treated with PFT-X in these field trials. The incidence of the surface browning type of sunburn ("buckskin") was surprisingly decreased by 79%. Total sunburn was surprisingly decreased by 73% in apples treated in accordance with the disclosure.

TABLE 2

Incidence of Sunburn Necrosis and Sunburn Browning as Influenced by PFT-X Formulation

| Fruit Variety | Observation Date | Incidence of Necrosis | | Incidence of Browning | |
|---|---|---|---|---|---|
| | | Control | Treated | Control | Treated |
| 'Jonagold' | 14 Jul. 1997 | 0[1] | 0 | 0 | 0 |
| | 29 Jul. 1997 | 6.7 | 5.0 | 6.7 | 0 |
| | 19 Aug. 1997 | 26.3 | 9.1* | 17.5 | 3.6* |
| | 10 Sep. 1997 | 25.9 | 8.8* | 6.9 | 0 |

[1]Each mean represents observations on 60 attached fruit that had been fully exposed to solar radiation for a daily duration of 3 hours before to 3 hours after solar noon. Controls recieved no application of the test formulation. Treated apples recieved one application of formulation.
*Denotes statistical significance of differences between control and treatment for each date as determined by a Yates-corrected z-test at the 0.05 level with n = 60.

EXAMPLE 2

The beneficial effects of a representative protective composition of the disclosure in decreasing sunburn in field trials on 5-year-old 'Jonagold' apples are shown in Table 3. The PFT-X composition was as listed in Table 2, but the formulation was diluted 1:1 with water before application to trees. Treatments were applied to single tree plots replicated ten times in a completely randomized design in the Clayton Orchard near Orondo, Wash. All treatments were applied with a handgun sprayer at approximately 150 pounds per square inch (psi) to near the point of drip, simulating a dilute spray of approximately 200 gallons/acre. For PFT-X, this provided 40 pounds of organoclay per acre and for Surround®, this provided 50 pounds of kaolin per acre. Each formulation was applied three times during the 1999 fruit growing season on July 7, August 4, and September 1. The control trees were sprayed with water on the same dates. For comparison, Surround®, a kaolin-based formulation containing proprietary surfactants and spreaders (marketed on a limited scale in 1999 by Engelhard Chemical Co., Iselin, N.J.) was applied in the same manner to another group of trees. Surrounds was formulated as suggested by the manufacturer using M-03, a proprietary Spreader/Sticker. 450 ml of M-03 was added to 50 lbs of kaolin clay (Engelhard Chemical M-97-009) that had previously been added to 100 gallons of water in a recirculating sprayer tank.

The sunburn data are presented in Table 3. The incidence of sunburn in all treatments was evaluated on August 31 by evaluating all fruit on each tree in the experiment. The percent of sunburn incidence for each tree was calculated. Both sunburn necrosis and sunburn browning were evaluated, but the incidence of sunburn necrosis was so low (<7% of total sunburn) that the two types were combined and analyzed statistically. Data were transformed using the angular or inverse sine transformation method (Steel and Torrie, Principles and Procedures of Statistics, McGraw-Hill Book Co., Inc., New York) prior to an analysis of variance.

TABLE 3

Incidence of Sunburn as Influenced by PFT-X.

| | Incidence of Sunburn (%) | | |
|---|---|---|---|
| Fruit Variety | Control | Treated with PFT-X | Treated with Surround ® |
| 'Jonagold' | 15.77 | 6.01** | 15.26 |

**Denotes statistical significance of differences between control and PFT-X at the 0.01 level.
Total number of fruit evaluated were 723, 649, and 557 for the control, PFT-X treated, and Surround ®-treated apples, respectively.

The data in Table 3 indicate that apples treated in accordance with the disclosure surprisingly showed significantly less sunburn than apples treated with water or Surround®.

EXAMPLE 3

The beneficial effects of a representative protective composition of the disclosure in decreasing sunburn in field trials on 3-year-old 'Cameo' apples are shown in Table 4. Sunburn damage was evaluated September 1. Other experimental details were the same as those in Example 2 except that trees were smaller, and two trees were included in each replication. The trees were in the Fleming Orchard near Orondo, Wash.

TABLE 4

Incidence of sunburn as influenced by PFT-X Application

| | Incidence of Sunburn (%) | | |
|---|---|---|---|
| Fruit Variety | Control | Treated with PFT-X | Treated with Surround ® |
| 'Cameo' | 13.40 | 6.59** | 13.85 |

**Denotes statistical significance of differences between control and PFT-X at the 0.01 level.
Total number of fruit evaluated were 291, 260, and 258 for the control, PFT-X treated, and Surround ®-treated apples, respectively.

The incidence of sunburn in 'Cameo' apples was surprisingly reduced significantly when treated with the disclosed PFT-X formulation as compared to apples treated with water or Surround® (Table 4).

EXAMPLE 4

The beneficial effects of a representative protective composition of the disclosure in decreasing sunburn in field trials on 9-year-old 'Fuji' apples are shown in Table 5. Sunburn damage was evaluated October 19. Other experimental details were the same as those in Example 2 except that a fourth application of formulations was made September 29. All fruit on two large branches of each tree were evaluated, as trees were much larger than those used in Examples 2 and 3. The trees were in the Fugachee Orchards near Pateros, Wash.

TABLE 5

Incidence of sunburn as influenced by PFT-X Application

| Fruit Variety | Incidence of Sunburn (%) | | |
|---|---|---|---|
| | Control | Treated with PFT-X | Treated with Surround ® |
| 'Fuji' | 14.85 | 2.44** | 8.59 |

**Denotes statistical significance between PFT-X and both control and Surround ® at the 0.01 level.
Total number of fruit evaluated were 485, 779, and 489 for the control, PFT-X treated, and Surround ®-treated apples, respectively.

The incidence of sunburn in 'Fuji' apples was surprisingly reduced significantly when treated with the disclosed PFT-X formulation as compared to apples treated with water or Surround® (Table 5).

EXAMPLE 5

To evaluate the entomological efficacy of the disclosed formulation PFT-X, a trial was conducted with 12-year-old 'Gala' apple trees at the Washington State University Tree Fruit Research & Extension Center, Wenatchee, Wash. Control of codling moth (*Cydia pomonella* L.)(CM) during their second generation was evaluated. PFT-X treatments were applied to single tree plots replicated five times in a randomized complete block. PFT-X was applied with a handgun sprayer at 300 psi to the point of drip, simulating a dilute spray of approximately 400 gallons/acre. Three different PFT-X and Surround® application protocols were tested:

1) trees were sprayed with PFT-X or Surround® three times during the CM oviposition period (July 19 [1,000 degree day total], July 27 and August 4); 2) trees were sprayed with PFT-X or Surround® three times during the CM hatch period (August 12 [1,250 degree day total], August 18 and 25); and 3) trees were sprayed with PFT-X or Surround® six times (all dates) covering the CM oviposition and hatch periods. For all PFT-X and Surround® application protocols a sample of fruits was harvested and an evaluation of CM insect damage to the fruit was made on September 1 by visually inspecting fifty apples per replicate and recording the number of stings and entries.

TABLE 6

Codling Moth damage to apple fruit as influenced by applications of PFT-X or Surround ® during oviposition, hatch, or oviposition + hatch.

| Treatment | Rate (Form./ 100 gal) | Timing[1] | #/50 fruit | | % total injury |
|---|---|---|---|---|---|
| | | | Stings | Entries | |
| Surround ® | 25 lbs | Oviposition | 0.8a[2] | 3.0bc | 7.6b |
| Surround ® | 25 lbs | Hatch | 0.8a | 4.0b | 9.6b |
| Surround ® | 25 lbs | Oviposition + hatch | 0.8a | 2.0bc | 5.6b |
| PFT-X | 20 lbs | Oviposition | 0.8a | 2.6bc | 6.8b |
| PFT-X | 20 lbs | Hatch | 1.2a | 2.2bc | 5.2b |
| PFT-X | 20 lbs | Oviposition + hatch | 1.4a | 0.2c | 3.2b |
| Untreated | NONE | | 0.8a | 12.2a | 26.0a |

[1]Application dates for Oviposition timing were Jul. 19, Jul. 27 and Aug. 4 and for the Hatch timing were Aug. 12, 18, and 25. Applications for the Oviposition + hatch timing included all six dates.
[2]Means in the same column followed by the same letter not significantly different (P = 0.05, Duncan's new multiple range test).

Both the PFT-X and Surround® treatments significantly reduced CM injury relative to the untreated control (Table 6). There was no difference in the number of CM stings (shallow unsuccessful entries) across treatments. Most of the effect of the treatments with both PFT-X and with Surround® was observed in the reduction of successful entries into fruit. There was no observed advantage of timing, but when applications were made to both the oviposition and hatch periods, the level of fruit injury was slightly lower than when treatments were applied to either the oviposition or hatch period. The formulations of the present disclosure surprisingly show promise as tools to manage codling moth, probably as supplements to other "soft" tactics such as mating disruption. These data and the data presented in Tables 1-4 demonstrate that the disclosed composition surprisingly has dual benefits when applied to fruit trees. The disclosed composition is surprisingly effective at significantly reducing the incidence of fruit sunburn and reducing fruit damage caused by codling moth.

EXAMPLE 6

Some formulations cause phytotoxicity and others affect physiological processes such as photosynthesis when applied to trees. It has been shown that any unusual change in the overall bioenergetic status of the plant can be detected by a change in chlorophyll fluorescence (See generally, Lichtenthaler, K. K., "Applications of Chlorophyll Fluorescence in Photosynthesis Research, Stress Physiology," Hydrobiology and Remote Sensing, Kluwer Academic Publishers, Dordrecht, Germany (1988)). This includes all the reactions from the oxidation of water through electron transport, development of the electrochemical gradient, ATP synthesis, and eventually the series of enzymatic reactions for CO2 reduction to carbohydrate in the leaf. Even changes in the plant that affect stoma opening and gas exchange with the atmosphere are reflected by changes in the fluorescence characteristics of a leaf. Therefore fluorescence was used as an indicator of any deleterious effects resulting from application of formulation. An OS5-FL Modulated Chlorophyll Fluorometer (Opti-Sciences, Inc. Tyngsboro, Mass.) was used to determine 'dark-adapted' Fv/Fm. $Fv/Fm = Fm - Fo/Fm$ where Fo and Fm are the minimal and maximal fluorescence yield of a 'dark adapted' sample. Fluorescence was determined on five attached leaves on trees in each of the five replications used in Example 4. On average, 84% of the incident quanta are absorbed by a leaf. Thus, a value for Fv/Fm of about 0.8 indicates healthy leaves with near maximal electron transport.

TABLE 7

Influence of PFT-X and Surround ® on fluorescence of leaves (estimation of electron flow in Photosystem II of photosynthesis). Same trees and treatments used in Example 4 were tested.

| Treatment | Rate (Form./ 100 gal) | Application Dates | Fluorescence (Fv/Fm) |
|---|---|---|---|
| Surround ® | 25 lbs | Jul. 19, Jul. 27, Aug. 4 | 0.777 |
| Surround ® | 25 lbs | Aug. 12, 18, and 25 | 0.797 |
| Surround ® | 25 lbs | Jul. 19, 27; Aug. 4, 12, 18, 25 | 0.816 |
| PFT-X | 20 lbs | Jul. 19, July 27, Aug. 4 | 0.808 |
| PFT-X | 20 lbs | Aug. 12, 18, and 25 | 0.781 |
| PFT-X | 20 lbs | Jul. 19, 27; Aug. 4, 12, 18, 25 | 0.785 |
| Untreated | NONE | | 0.801 |

The results in Table 7 indicate that the disclosed formulation had no significant effect on (P=0.05) fluorescence of the leaves to which formulation was applied. Thus, surprisingly no evidence of damage to the overall bioenergetic status of the trees is seen with any of the formulations and no phytotoxicity to either fruit or leaves was observed with any formulations.

EXAMPLE 7

Before field testing, entomologists sometimes conduct bioassays to determine the inherent toxicity of new formulations, changes in behavior of insects exposed to new formulations, and appropriate concentrations to apply. Accordingly, the disclosed PFT-X formulation was used in two bioassays.

Adulticide bean disk bioassay. Leaf disks (2 cm diameter) were cut from untreated leaves of bean (*Phaseolus vulgaris* 'Henderson Bush'). Disks were floated with the abaxial (lower) surface up in a ¾ ounce plastic portion cup filled with cotton and distilled water. Twenty adult twospotted spider mites (TSM), (*Tetranychus urticae* Koch) were transferred to the lower surface with a fine paintbrush. The leaf disks containing mites were treated with five concentrations of PFT-X or a distilled water check.

All cups containing the five replicates of each treatment were treated at the same time in a Potter Spray Tower equipped with the intermediate nozzle, and set to 6.5 psi. Two ml of the pesticide solution were placed in the reservoir, and sprayed onto the disks. The mites were held in a growth chamber at 22+/−2 degrees C. Mites were evaluated variously from 24 h after treatment for response as described immediately below.

Category Description Alive Moving without stimulation, or capable of moving >1 body length after gentle stimulation with brush. Dead No movement whatsoever, even after stimulation; or desiccated. Moribund Capable of producing some movement, especially twitching of legs, but unable to move >1 body length after stimulation. Runoff Found in cotton or water surrounding leaf surface, but not on leaf disk. Makes no difference if dead or alive. (If walk off occurs during the course of the evaluation, count as alive.)

Table 8 presents the results obtained using the bean disk bioassay and PFT-X at a variety of application doses.

TABLE 8

Mortality and runoff resulting from treatment of twospotted spider mites on bean disks treated with PFT-X. PFT-X was applied Jun. 29, 1999, and the evaluation was done Jun. 30. The full-strength PFT-X as described in Table 1 was diluted in distilled water to provide concentrations ranging from 100 to 700 grams of PFT-X per liter.

| Concentration (g/liter) | No. Subjects | % Mortality | % Runoff |
|---|---|---|---|
| 700 | 111 | 7.3 | 1.0 |
| 500 | 103 | 3.8 | 3.5 |
| 300 | 99 | 0.0 | 4.6 |
| 200 | 101 | 2.9 | 1.9 |
| 100 | 102 | 4.9 | 0.0 |
| 0 | 103 | 4.5 | 4.6 |

The results in Table 8 indicate that there was no dose response to the disclosed PFT-X formulation after 24 h, either in terms of mortality or runoff.

Motile Stage Mortality and Behavior, Whole Plant Bioassay: Five leaves on each of six infested bean plants from the composite TSM colony were tagged. Prior to treatment, all motile stages were counted with a 5.times.-magnification headband (OptiVisor). Counts from the top and bottom side of the leaf were recorded separately. The same leaves were counted 24 h after treatment. Various concentrations of PFT-X were applied with a hand-pump-pressurized sprayer. The suspensions were kept under constant agitation during application. Five replicates were used for each treatment. Table 9 shows the data obtained from the whole plant bioassays with the disclosed PFT-X formulation applied at a variety of concentrations. Primary data were analyzed using the General Linear Models Procedure of SAS (SAS 1988 (Statistical Analysis Institute, 1988; SAS/Stat User's Guide, Release 6.03 Edition; SAS Institute, Inc., Cary, N.C.)) using both a classification model (AOV) and numeric (regression).

TABLE 9

Location and mortality status of mites before and after treatment with the inventive formulation in a whole bean plant bioassay. PFT-X was diluted as described in Table 7, and applied Jun. 30, 1999. Pre-treatment observations were made before application on June 30, and post-treatment observations were made on Jul. 1, 1999. Means in the same column followed by the same letter not significantly different.

| | | Live | | | Dead | |
|---|---|---|---|---|---|---|
| Concn in g/liter | Total live mites/ leaf | Total surface mites/ leaf | Bottom surface mites/ leaf | Top surface % mites | Top surface mites/ leaf | Bottom surface mites/ leaf |
| Pretreatment | | | | | | |
| 700 | 35.6a | 5.8a | 29.8a | 17.2 | — | — |
| 500 | 33.6a | 4.8a | 28.8a | 15.9 | — | — |
| 300 | 35.8a | 8.4a | 27.4a | 22.2 | — | — |
| 200 | 35.6a | 8.0a | 27.6a | 23.6 | — | — |
| 100 | 38.2a | 9.8a | 28.4a | 30.4 | — | — |
| 0 | 29.0a | 12.6a | 16.4a | 42.9 | — | — |
| Post-treatment | | | | | | |
| 700 | 7.2a | 2.4a | 4.8a | 28.7 | 3.8 | 3.8 |
| 500 | 11.4a | 3.8a | 7.6a | 36.4 | 2.2 | 4.0 |
| 300 | 6.8a | 1.8a | 5.0a | 25.0 | 4.0 | 4.2 |
| 200 | 14.6a | 4.2a | 10.4a | 27.7 | 2.8 | 2.4 |
| 100 | 12.2a | 3.2a | 9.0a | 22.5 | 2.6 | 5.4 |
| 0 | 14.0a | 6.6a | 7.4a | 42.6 | 4.8 | 3.6 |

Although there was a considerable decrease in mite population after treatment with PFT-X, this decrease was not related to concentration. No differences among the various concentrations of PFT-X occurred in any of the variables measured or calculated (Table 9). In addition to mortality, the behavior of the mites (i.e., occupation of the upper versus lower surface of the leaf) was observed. Normally, the TSM preferentially occupy the lower leaf surface, and most of the webbing is found there. Treatment with the PFT-X did not alter this pattern (Table 9). The relationship between concentration and percentage occupancy on the upper leaf surface was analyzed by regression analyses, but no significant relationship existed after the treatment (data not shown). In summary, PFT-X surprisingly does not appear to affect either mortality or one aspect of behavior (leaf surface preference) of these mites.

EXAMPLE 8

The effects of the disclosed formulation (PFT-X) on phytophagous mites and their natural enemies were examined in an apple orchard. Four-year-old 'Oregon Spur Delicious' apples were used. Treatments were applied with an air-blast sprayer calibrated to deliver 100 gallons per acre. PFT-X treatments were applied August 4. The plot originally had no mite populations, so the orchard was seeded with twospotted mites (*Tetranychus urticae* Koch) from a greenhouse colony and later with European red mites (*Panonychus ulmi* Koch) from another orchard. In addition, the plot was sprayed with Asana® 0.66EC (DuPont Co., Wilmington, Del.)(1 pint/acre) plus Lorsban® 50W (Dow Chemical, Midland, Mich.)(3 lbs/acre) to reduce codling moth populations in the plots. Post-treatment mite counts were taken every week until early fall. A sample of 20 leaves per plot was taken and kept cool during transportation to the laboratory. Mites were removed from the leaves with a leaf-brushing machine, and collected on a revolving sticky glass plate. Mites on the plate were counted with the aid of a stereoscopic microscope. Motile and egg stages of the pest mites European red mite, twospotted spider mite, and McDaniel spider mite (*Tetranychus mcdanieli* McGregor) were counted, along with motile and egg stages of the predatory mites *Typhlodromus occidentalis* (Nesbitt) and Zetzellia mail (Ewing). Motile stages only of apple rust mite, *Aculus schlechtendali* (Nalepa), were also counted. The eggs of twospotted spider mite and McDaniel mite could not be distinguished from one another, and were recorded as a single category (Tetranychus eggs).

Table 10 presents the phytophagous and predatory mite population data and the effects of spray applications of various formulations including the disclosed PFT-X composition.

TABLE 10

Phytophagous and predatory mite populations before and after treatment with miticides and formulations.

| Treatment | Rate/ acre | Aug. 2 | Aug. 11 | Aug. 17 |
|---|---|---|---|---|
| | | Total tetranychids/leaf | | |
| PFT-X | 10 lbs. | 6.99a[1] | 6.92a | 20.51a |
| PFT-X | 20 lbs. | 7.75a | 9.95a | 10.04a |
| Surround ® | 25 lbs. | 6.74a | 23.01a | 19.24a |
| Surround ® | 50 lbs. | 13.51a | 8.91a | 22.13a |
| Orchex 796[2] | 1% | 9.09a | 21.25a | 6.70a |
| Pyramite ® 60W[3] + Orchex 796 | 4.4 oz. + 0.25% | 8.14a | 5.83a | 11.89a |
| Check | — | 7.16a | 13.93a | 29.98a |
| | | Total predatory mites/leaf | | |
| PFT-X | 10 lbs. | 0.13a | 0.13a | 1.30a |
| PFT-X | 20 lbs. | 0.00a | 3.59a | 0.00a |
| Surround ® | 25 lbs. | 0.10a | 3.43a | 0.29a |
| Surround ® | 50 lbs. | 0.00a | 0.04a | 0.38a |
| Orchex 796 | 1% | 0.00a | 0.79a | 0.75a |
| Pyramite ® 60W + Orchex 796 | 4.4 oz. + 0.25% | 0.03a | 1.04a | 0.09a |
| Check | — | 0.18a | 0.09a | 0.33a |

[1]Data were analyzed using analysis of variance on each count date (PROC GLM; SAS Institute, 1988). Means were separated with the Waller-Duncan k-ratio t-test.
[2]Purchased from Exxon Company, U.S.A., Houston, TX.
[3]Purchased from BASF Agriculture Products, Research Triangle Park, NC.

The mite populations consisted primarily of twospotted mites (71% overall) with some European red mite, and occasionally, some McDaniel mite forming a proportion of the population. The predatory mite population was primarily *T. occidentalis* (82% overall), with the remainder of the population comprised of *Z. mali*. Populations began to rise in late July, and were at an appropriate level (3 to 8 mites/leaf) by early August. No statistical differences occurred among any of the treatments (including the untreated check) at any time during the course of the experiment, despite treatment means that ranged from 7 to 30 mites/leaf (Table 10).

Predatory mite populations were high but variable throughout the test. On the first post-treatment count date (August 11), the low rate of Surround® and the high rate of PFT-X had exceptionally high *T. occidentalis* populations (Table 10). This is especially notable since Asana®, a chemical known for its toxicity to predatory mites, was being sprayed at intervals. The use of Asana® compromised the test for predator toxicity, but there was no evidence that any of the materials were acutely toxic to *T. occidentalis* and *Z. mali*.

An additional mite control variable, known as cumulative mite days (CMD) was calculated for the formulations indicated in Table 10. CMD was calculated for each formulation using the equation:

$$CMD = \Sigma 0.5(pop_1 + pop_2)(date_1 - date_1),$$

where pop-1 is the population (total tetranychids/leaf) on date-1 and pop-2 is the population (total tetranychids/leaf on date-2).

CMD represents a time-weighted measurement of the populations. The CMD for Pyramite®+Orchex (CMD=402) was lowest. The CMD was 423 for PFT-X (10 lbs./A), and 477 for PFT-X (20 lbs./A). The CMD for the check was 567. The CMD was 508 for Surrounds (50 lbs./A) and 519 for Surround® (25 lbs./A). For Orchex 796, the CMD was 513. The CMD data above indicate that PFT-X seemed to provide some suppression of the leaf mite populations across the growing season.

In summary, the disclosed formulation of PFT-X tested in Table 10 surprisingly had no apparent toxicity on the mites or their predators. PFT-X did not cause mortality in the mites. However, it is particularly important that the disclosed formulation does not kill the beneficial predators or repel them from the leafs surface, as this result indicates that PFT-X will be useful in Integrated Pest Management (IPM). In IPM practices, a formulation is useful only if the formulation provides what is called "soft suppression" of pests. That is, the IPM formulation does not cause a significant disruption to the natural control processes by, for example, negatively impacting populations of beneficial organisms.

EXAMPLE 9

The effects of several formulations on leafhopper nymphs in an apple orchard (cv. 'Braeburn') near Quincy, Wash. were examined. Four replicates were used where each replicate consisted of three trees in a single row. Leafhopper nymphs were sampled by counting the nymphs on 20 leaves/tree. Populations were sampled weekly until the majority of the population had transformed to the adult stage. A single-spray program and a three-spray program were compared. The single-spray treatment and the first application of the three-spray program were applied on August 3, using a multiple tank air-blast sprayer calibrated to deliver 100 gallons/acre. The second and third sprays of the three-spray program were applied on August 12 and August 20. Table 11 presents the data obtained from this study.

TABLE 11

Leafhopper nymph populations before and after treatment with pesticides and formulations.

| Treatment | Rate/acre | No. appl. | Leafhopper nymphs/leaf | | | | | |
|---|---|---|---|---|---|---|---|---|
| | | | July 29 | Aug 6 | Aug 9 | Aug 16 | Aug 23 | Aug 31 |
| PFT-X | 20 lbs | 1 | 3.89a[1] | 1.99bcd | 0.91c | 3.86abc | 3.55ab | 1.10ab |
| PFT-X | 20 lbs | 3 | 3.54a | 2.81bc | 2.85a | 3.49abc | 3.40ab | 1.21ab |
| Surround ® | 50 lbs | 1 | 3.44a | 1.86bcd | 1.09bc | 2.38bc | 2.63ab | 1.36a |
| Surround ® | 50 lbs | 3 | 3.49a | 1.41cd | 1.08c | 1.88c | 2.01bc | 0.31b |
| Orchex 796 | 1% | 1 | 3.44a | 3.28b | 3.36a | 5.01ab | 4.15a | 1.65a |
| Pyramite ® 60W + Orchex 796 | 4.4 oz + 0.25% | 1 | 3.53a | 1.34cd | 2.46ab | 5.09ab | 3.73ab | 1.44a |
| Provado ® L6F[2] + Sylgard 309[3] | 6 fl oz + 4 fl oz | 1 | 3.70a | 0.61d | 0.20c | 1.18c | 0.60c | 0.94ab |
| Check | — | — | 3.70a | 6.11a | 3.79a | 6.28a | 4.24a | 1.85a |

[1]Data were analyzed using analysis of variance on each count date (PROC GLM; SAS Institute, 1988). Means were separated with the Waller-Duncan k-ratio t-test. Means within columns not followed by the same letters are significantly different.
[2]Purchased from Bayer Corporation, Pittsburgh, PA.
[3]Purchased from Wilfarm, L.L.C., Gladstone, MO.

The disclosed PFT-X formulation (single application on August 3) provided suppression of nymphs through August 9, but thereafter the population mean was not different from the check (Table 11). With the three-spray program, PFT-X significantly suppressed nymph populations only on August 6, although the population means for the nymphs were always lower than the check. Only the standard (Provado+Sylgard) provided much knockdown and residual control.

Orchex 796, an oil used by some in IPM programs as a soft pesticide, was included in this test. It was different than the check only on August 6. Its suppression of nymph populations was therefore much like that of the disclosed PFT-X formulation. Thus, the data presented in Table 11 indicate that the PFT-X formulation of the present disclosure surprisingly can be used as a component of an integrated pest management program.

EXAMPLE 10

The beneficial effects of a representative protective composition of the disclosure in decreasing damage by deleterious insects to foliage and fruit was tested in field trials on (A) apples [cv. 'Delicious', 'Golden Delicious', 'Fuji', 'Cameo', 'Jonagold' and 'Gala'] with the following target insects: codling moth, leafrollers, leafhoppers, spider mites, aphids, leafminers, true bugs (Pentatomidae and Miridae), cutworms, fruit worms, apple maggot, cherry fruit fly and San Jose scale; and on (B) pears [cv. 'Bartlett' and 'd'Anjou'] with the following target insects: pear psylla, true bugs, cutworms, spider mites, mealybug, and codling moth. Initial tests were conducted with high-pressure handgun spray equipment using a spray volume equivalent to 100 to 400 gal/acre. The results obtained allow determination of an activity profile for the disclosed formulation on the target insects. Increasing concentrations of Tixogel® MP100 from 1 to 5% in APL-BRITE 310 C were used with aqueous dilutions of 1/2 to 1/10 strength to arrive at appropriate concentrations. Treatments were replicated three to six times in a randomized complete block design with single trees or small blocks of trees. An appropriate control consisted of trees that received no spray treatments. For entomological evaluations of pests on foliage, populations of insects such as mites, aphids, leafhoppers, pear psylla, and leafminers are evaluated pre-treatment and at intervals in the post-treatment period to determine efficacy. For pear psylla and other pests such as the codling moth, scale, and leafrollers, the level of injury to fruit was evaluated at three times during the growing season in each treatment by checking at least 25 fruit per tree (replicate).

While a preferred embodiment of the invention has been illustrated and described, it will be appreciated that various changes can be made therein without departing from the spirit and scope of the invention.

The embodiments of the invention in which an exclusive property or privilege is claimed are defined as follows:

1. A fruit or vegetable coated with a plant protective coating comprising a protective agent, a wax emulsion, and a lipophilic thixotropic smectic clay, wherein the protective agent is selected from the group consisting of fungicides, bactericides, insecticides, and mixtures thereof, wherein the wax emulsion comprises a matrix of complex hydrocarbons, an anionic lipophilic emulsifier, an ionic hydrophilic emulsifier and water, wherein the anionic lipophilic emulsifier is selected from the group consisting of oleic acid, stearic acid and mixtures thereof, wherein the ionic hydrophilic emulsifier is selected from the group consisting of ethanolamine, diethanolamine, triethanolamine, alkyl alcohol amine, morpholene and mixtures thereof.

2. The fruit or vegetable of claim 1 wherein the wax emulsion comprises an edible synthetic oxygen containing wax.

3. The fruit or vegetable of claim 1 wherein the plant protective coating comprises about 0.5 to 10% (weight/weight) lipophilic thixotropic smectic clay and about 90 to 99.5% wax emulsion.

4. The fruit or vegetable of claim 3 wherein the protective coating mixture plant protective coating is diluted into an aqueous solution in a volume/volume ratio of from about 1 part plant protective coating mixture to about 1 part aqueous solution to about 1 part plant protective coating mixture to 10 parts aqueous solution.

5. The fruit or vegetable of claim 1 wherein the matrix of complex hydrocarbons comprises a wax mixture comprising long chain fatty acids and long chain esters.

6. The fruit or vegetable of claim 5 wherein the wax mixture is a natural wax selected from the group consisting of Carnauba wax, Candelilla wax, Alfa wax, montan wax, rice-bran wax, beeswax, Japan wax and mixtures thereof.

7. The fruit or vegetable of claim 1 wherein the fruit or vegetable is a citrus fruit.

8. A plant protective composition comprising: about 0.05 to 1.0% (weight/volume) copper formulation, about 0.5 to 10% (weight/weight) lipophilic thixotrophic smectic clay, and about 90 to 99.5% (weight/weight) wax emulsion, said emulsion comprising: about 5 to 10% (weight/weight) natural wax selected from the group consisting of Carnauba wax, Candelilla wax, Alfa wax, montan wax, rice-bran wax, beeswax, Japan wax and mixtures thereof; about 1 to 15% (weight/weight) oleic acid; about 1 to 15% (weight/weight) morpholene; and about 60 to 93% water.

9. A fruit or vegetable coated with the plant protective composition of claim 8.

10. The fruit or vegetable of claim 9 wherein the fruit or vegetable is an orange or grapefruit.

11. A method of protecting a plant from disease and insect damage comprising spraying a plant with an insect-controlling amount of a plant protective composition comprising a protective agent and a wax emulsion, wherein the protective agent is selected from the group consisting of fungicides, bactericides, insecticides, and mixtures thereof, wherein the wax emulsion comprises a matrix of complex hydrocarbons, an anionic lipophilic emulsifier, an ionic hydrophilic emulsifier and water, wherein the anionic lipophilic surfactant is selected from the group consisting of oleic acid, stearic acid and mixtures thereof, wherein the ionic hydrophilic emulsifier is selected from the group consisting of ethanolamine, diethanolamine, triethanolamine, alkyl alcohol amine, morpholene and mixtures thereof.

12. A method of protecting a plant from disease and insect damage comprising spraying the plant with lipophilic thixotropic smectic clay, spraying a plant with an insect-controlling amount of a plant protective composition comprising a protective agent and a wax emulsion, wherein the protective agent is selected from the group consisting of fungicides, bactericides, insecticides, and mixtures thereof, wherein the wax emulsion comprises a matrix of complex hydrocarbons, an anionic lipophilic emulsifier, an ionic hydrophilic emulsifier and water, wherein the anionic lipophilic surfactant is selected from the group consisting of oleic acid, stearic acid and mixtures thereof, wherein the ionic hydrophilic emulsifier is selected from the group consisting of ethanolamine, diethanolamine, triethanolamine, alkyl alcohol amine, morpholene and mixtures thereof.

\* \* \* \* \*